(12) United States Patent
Li

(10) Patent No.: US 10,405,563 B2
(45) Date of Patent: Sep. 10, 2019

(54) COMPOSITIONS AND METHODS FOR MODULATING GASTROINTESTINAL MICROFLORA IN A CANINE

(71) Applicant: Nestec SA, Vevey (CH)

(72) Inventor: Qinghong Li, Chesterfield, MO (US)

(73) Assignee: Sociate des Produits Nestle SA, Vevey (CH)

(*) Notice: Subject to any disclaimer, the term of this patent is extended or adjusted under 35 U.S.C. 154(b) by 0 days.

(21) Appl. No.: 15/686,893

(22) Filed: Aug. 25, 2017

(65) Prior Publication Data

US 2018/0064140 A1 Mar. 8, 2018

Related U.S. Application Data

(60) Provisional application No. 62/382,923, filed on Sep. 2, 2016.

(51) Int. Cl.

| | |
|---|---|
| *A01N 63/00* | (2006.01) |
| *A61K 49/00* | (2006.01) |
| *A01N 65/00* | (2009.01) |
| *A23K 50/40* | (2016.01) |
| *A23K 20/147* | (2016.01) |
| *A23K 20/158* | (2016.01) |
| *A23K 20/10* | (2016.01) |
| *A61K 35/741* | (2015.01) |
| *A23K 10/16* | (2016.01) |
| *A23K 10/18* | (2016.01) |
| *A61K 35/00* | (2006.01) |

(52) U.S. Cl.
CPC .............. *A23K 50/40* (2016.05); *A23K 10/16* (2016.05); *A23K 10/18* (2016.05); *A23K 20/10* (2016.05); *A23K 20/147* (2016.05); *A23K 20/158* (2016.05); *A61K 35/741* (2013.01); *A61K 2035/115* (2013.01)

(58) Field of Classification Search
CPC ........ A61K 49/00; A61K 47/00; A61K 39/00; A61K 39/02
USPC ................................ 424/9.1, 9.2, 93.1, 93.3
See application file for complete search history.

(56) References Cited

U.S. PATENT DOCUMENTS

| 9,040,101 B2 | 5/2015 | Heiman et al. |
| 2015/0275275 A1 | 10/2015 | Ehrlich et al. |

FOREIGN PATENT DOCUMENTS

| EP | 1474171 B1 | 4/2008 |
| EP | 1633202 B1 | 11/2008 |
| WO | 200195739 A2 | 12/2001 |
| WO | 2003061705 A1 | 7/2003 |
| WO | 2004107878 A1 | 12/2004 |
| WO | 2012024638 A2 | 2/2012 |

OTHER PUBLICATIONS

Backhed, F., et al. "Defining a healthy human gut microbiome: current concepts, future directions, and clinical applications" Cell Host. Microbe, 2012, 12, 611-622.
Lambrecht K.J. "Effective strategies, dialogues and tools for a successful weight-management program", Proceedings of Companion Animal Nutrition Summit, 2015, pp. 67-76.
Cho, I., Blaser, M.J., "The human microbiome: at the interface of health and disease" Nat. Rev. Genet. 2012, 13, pp. 260-270.
Clemente, J.C., et al., "The impact of the gut microbiota on human health: an integrative view," Cell, 2012, 148, 1258-1270.
Duca, F., et al. "Metabolic interplay between gut bacteria and their host," Front Horm. Res. 2014, 42, 73-82.
Gerard, P., "Gut microbiota and obesity" Cell Mol. Life Sci. 2015.
Kealy, R.D., et al. "Effects of diet restriction on life span and age-related changes in dogs" J. Am. Vet. Med. Assoc. 2002, 220, 1315-1320.
Le Roy et al. "Intestinal microbiota determines development of non-alcoholic fatty liver disease in mice" Gut, 2013, 62, 1787-1794.
Ley, R.E., et al. "Obesity alters gut microbial ecology" Proc. Natl. Acad. Sci. U. S. A, 2005, 102, 11070-11075.
Ley, R.E., et al. "Microbial ecology: human gut microbes associated with obesity" Nature, 2006, 444, 1022-1023.
Mayer, E.A., et al. "Gut/brain axis and the microbiota" J. Clin. Invest, 2015, 125, 926-938.
Peeters, A., et al. "Obesity in adulthood and its consequences for life expectancy: a life-table analysis" Ann. Intern. Med., 2003, 138, 24-32.
Ridaura, V.K., et al. "Gut microbiota from twins discordant for obesity modulate metabolism in mice" Science, 2013, 341, 1241214.
Tremaroli, V., et al. "Functional interactions between the gut microbiota and host metabolism" Nature 2012. 489, 242-249.
Turnbaugh, P.J., et al. A"n obesity-associated gut microbiome with increased capacity for energy harvest" Nature 2006. 444, 1027-1031.
Ingrid Hang: "Effects of diet on the intestinal microbiota bacteria-derived metabolites and digestive enzymes in healthy dogs", Jan. 9, 2015, pp. 1-102, Retrieved from the internet https://helda.helsinki.fi/bitstream/handle/10138/152689/Effectso.pdf.
Ingrid Hang: "Effect of high contents of dietary animal-derived protein or carbohydrates on canine faecal microbiota", BMC Veterinary Research, Biomed Central, London GB, 2012 8:90.
Beloshapka, Alison N, et al. "Fecal microbial communities of healthy adult dogs fed raw meat-based diets with or without inulin or yeast cell wall extracts as assessed by 454 pyrosequencing" FEMS Microbiology Ecology, vol. 84, No. 3, 2013 pp. 532-541.
Burkholder, W J, et al: "Timely Topics in Nutrition, Foods, and Techniques for Managing Obesity in Companion Animals," Journal of the American Veterinary Medical Association, US, vol. 212, No. 5, Jan. 1, 1988, pp. 658-662.

(Continued)

*Primary Examiner* — Rodney P Swartz
(74) *Attorney, Agent, or Firm* — Ronald A. Burchett

(57) ABSTRACT

The present invention relates to methods and compositions for modulating gastrointestinal microflora of a canine. In one embodiment, a method of modulating gastrointestinal microflora in a canine can comprise administering to the canine a pet food composition comprising from about 25% to about 60% protein, from about 5% to about 30% carbohydrates, fat, and fiber; where after administration, the *Bacteroidetes* to *Firmicutes* (B/F) ratio of the canine is less than 0.8.

15 Claims, No Drawings

(56) References Cited

OTHER PUBLICATIONS

Siobhan F. Clarke et al, "The Gut Microbiota and Its Relationship to Diet and Obesity: New Insights", Gut Microbes, vol. 3 No. 3, May/Jun. 2012 pp. 1186-202.
Silke Schmitz et al., "Understanding the canine intestinal microbiota and its modification by pro- , pre-, and symbiotics—what is the evidence?" Veterinary Medicine and Science, 2016(2) pp. 71-94.
H.-J. Park et al. "Association of Obesity with Serum Leptin, Adiponectin, and Serotonin and Gut Microflora in Beagle Dogs" Journal of Veterinary Internal Medicine, 2015 5;29, pp. 43-58.
International Search Report and Written Opinion PCT/IB2017/055140, dated Nov. 6, 2017.

COMPOSITIONS AND METHODS FOR MODULATING GASTROINTESTINAL MICROFLORA IN A CANINE

CROSS REFERENCE TO RELATED APPLICATIONS

This application claims priority to U.S. Provisional Application No. 62/382,923 filed Sep. 2, 2016, the disclosure of which is incorporated herein by this reference.

BACKGROUND

In the United States, over 50% of pets are either overweight or obese. Health risks associated with excessive body weight include diabetes, cardiovascular diseases, metabolic disorders, musculoskeletal disorders, cancer, and short life expectancy.

Trillions of microorganisms or microbes colonize the body surface and gastrointestinal (GI) track of their hosts to create a symbiotic relations. The intestinal microbiota plays an essential role in their hosts, including regulations of nutrient absorption, energy homeostasis including fat storage, lipogenesis and fatty acid oxidation and immune-system development. As a result, dysbiosis between the gut microbiota and their hosts have been associated with obesity and other metabolic disorders. More recently, imbalanced intestinal microbiotas have been implicated in many other health issues such as cardiovascular disease, immune disorders, and liver or brain disease. Modification of gut microbiota via nutrition management (e.g. prebiotics, probiotics) to restore the symbiosis with its host may provide various health benefits.

In both humans and rodents, research has suggested that increases in *Bacteroidetes* (B) to *Firmicutes* (F) ratio in gastrointestinal microbiota are beneficial to metabolic health. However, it is unclear the same is true in pets.

SUMMARY

The present disclosure relates generally to compositions and methods for modulating gastrointestinal microflora in a canine. In one embodiment, a method of modulating gastrointestinal microflora in a canine can comprise administering to the canine a pet food composition comprising from about 25% to about 60% protein, from about 5% to about 30% carbohydrates, fat, and fiber. Generally, after administration, the *Bacteroidetes* to *Firmicutes* (B/F) ratio of the canine is less than 0.8.

In another embodiment, a method of treating a canine for diabetes, obesity, an inflammatory disease, a cardiovascular disease, a metabolic disorder, a musculoskeletal disorder, or cancer, can comprise modulating the *Bacteroidetes* to *Firmicutes* (B/F) ratio of the canine to below 0.8.

Additional features and advantages are described herein and will be apparent from the following Detailed Description.

DETAILED DESCRIPTION

Definitions

As used in this disclosure and the appended claims, the singular forms "a," "an" and "the" include plural referents unless the context clearly dictates otherwise. Thus, for example, reference to "a composition" or "the composition" includes two or more compositions. The term "and/or" used in the context of "X and/or Y" should be interpreted as "X," or "Y," or "X and Y." Where used herein, the terms "example" and "such as," particularly when followed by a listing of terms, are merely exemplary and illustrative, and are not exclusive or comprehensive.

As used herein, "about" is understood to refer to numbers in a range of numerals, for example the range of −10% to +10% of the referenced number, within −5% to +5% of the referenced number, or in one aspect, within −1% to +1% of the referenced number, and in a specific aspect, within −0.1% to +0.1% of the referenced number. Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

All percentages expressed herein are by weight of the composition on a dry matter basis unless specifically stated otherwise. The skilled artisan will appreciate that the term "dry matter basis" means that an ingredient's concentration or percentage in a composition is measured or determined after any free moisture in the composition has been removed. When reference is made to the pH, values correspond to pH measured at 25° C. with standard equipment. An "amount" can be the total amount of the referenced component per serving of the composition or per distinct unit of the composition and/or can be the weight percentage of the referenced component by dry weight. Moreover, an "amount" includes zero; for example, the recitation of an amount of a compound does not necessarily mean that the compound is present, unless followed by a range that excludes zero.

The terms "food," "food product" and "food composition" mean a product or composition that is intended for ingestion by an animal and provides at least one nutrient to the animal. Further in this regard, these terms mean that the product or composition is in a form ready for consumption and is not merely an intermediate from which a consumable product or composition is made, although other food compositions can be added in some embodiments. The term "pet food" means any food composition intended to be consumed by a pet. The term "pet" means any animal which could benefit from or enjoy the compositions provided by the present disclosure. For example, the pet can be an avian, bovine, canine, equine, feline, hircine, lupine, murine, ovine, or porcine animal, but the pet can be any suitable animal.

The term "companion animal" means a dog or a cat. In an embodiment, the compositions and methods disclosed herein involve a senior dog. Dogs are considered senior in the last 25% of their lives. The life span of a dog depends on its size and/or its breed, but for the present disclosure a senior dog is a dog that is at least 5 years of age (e.g., at least 6 years of age, at least 7 years of age, or at least 8 years of age).

A "blended" composition merely has at least two components having at least one different characteristic relative to each other, preferably at least moisture content and water activity in the context of the present disclosure. In this regard, description of a composition as "blended" does not imply that the blended composition has been subjected to processing sometimes referenced as "blending," namely mixing components so that they are indistinguishable from each other, and, in one aspect, such processing is avoided when mixing one component with the other components to form a blended composition (e.g., mixing a dry component with a wet or semi-moist component). Further in this regard, in a blended composition each of the at least two components having at least one different characteristic relative to each other preferably retain their distinct identity and appearance.

"Wet food" means a pet food having a moisture content from about 50% to about 90%, and in one aspect, from about 70% to about 90%. "Dry food" means a pet food having a moisture content less than about 20%, and in one aspect, less than about 15%, and in a specific aspect, less than about 10%. "Semi-moist food" means a pet food having a moisture content from about 20% to about 50%, and in one aspect, from about 25% to about 35%.

"Kibbles" is used synonymously with "chunks" herein and both terms mean pieces of dry or semi-moist pet food which can have a pellet shape or any other shape and can be made by slicing a food composition into separate pieces. Non-limiting examples of kibbles include particulates; pellets; pieces of pet food, dehydrated meat, meat analog, vegetables, and combinations thereof; and pet snacks, such as meat or vegetable jerky, rawhide, and biscuits. A "meat analog" is a meat emulsion product that resembles pieces of natural meat in appearance, texture, and physical structure.

The term "effective amount" of "therapeutically effect amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In some aspects, the particular disease, condition, or disorder can be diabetes, obesity, an inflammatory disease, a cardiovascular disease, a metabolic disorder, a musculoskeletal disorder, or cancer.

The term "dietary supplement" means a product that is intended to be ingested in addition to the normal animal diet. Dietary supplements may be in any form, e.g., solid, liquid, gel, tablets, capsules, powder, and the like. In one aspect, they can be provided in convenient dosage forms. In some embodiments, they can be provided in bulk consumer packages such as bulk powders, liquids, gels, or oils. In other embodiments, supplements can be provided in bulk quantities to be included in other food items such as snacks, treats, supplement bars, beverages and the like.

The term "long-term administration" means periods of repeated administration or consumption in excess of one month. Periods of longer than two, three, or four months can be used for certain embodiments. Also, more extended periods can be used that include longer than 5, 6, 7, 8, 9, or 10 months. Periods in excess of 11 months or 1 year can also be used. Longer term use extending over 1, 2, 3, or more years are included in the invention. For certain aging animals, the animal will continue consuming on a regular basis for the remainder of its life. This can also be referred to as consumption for "extended" periods.

The term "regular basis" means at least monthly dosing with the compositions or consumption of the compositions, and in one aspect, means at least weekly dosing. More frequent dosing or consumption, such as twice or three times weekly, can be performed in certain embodiments. Still, in other embodiments, regimens can be used that comprise at least once daily consumption. The skilled artisan will appreciate that the B/F ratio may be a useful tool for assessing or determining dosing frequency. For example, for determining dosage or dosage frequency for pet food compositions or dietary supplements, the B/F ratio can be measured with the compositions modified or administration modified to achieve a specific desired ratio. A frequency, regardless of whether expressly exemplified herein, that allows maintenance of a B/F ratio within acceptable ranges can be useful herein. The skilled artisan will appreciate that dosing frequency will be a function of the composition that is being consumed or administered, and some compositions may require more or less frequent administration to maintain a desired B/F ratio.

The dosages expressed herein are in milligrams per kilogram of body weight per day (mg/kg/day) unless expressed otherwise.

The compositions disclosed herein may lack any element that is not specifically disclosed herein. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified. Any embodiment disclosed herein can be combined with any other embodiment disclosed herein unless explicitly and directly stated otherwise.

Embodiments

In an aspect of the present disclosure, a method of modulating gastrointestinal microflora in a canine can comprise administering to the canine a pet food composition comprising from about 25% to about 60% protein, from about 5% to about 30% carbohydrates, fat, and fiber. Generally, after administration, the *Bacteroidetes* to *Firmicutes* (B/F) ratio of the canine can be less than 0.8.

In another aspect, a method of treating a canine for diabetes, obesity, an inflammatory disease, a cardiovascular disease, a metabolic disorder, a musculoskeletal disorder, or cancer, can comprise modulating the *Bacteroidetes* to *Firmicutes* (B/F) ratio of the canine to below 0.8.

Additionally, the present methods can include identifying a distinct population of canines depending on the desired treatment. In one embodiment, the method can further comprise identifying a canine in need of B/F ratio modulation. Canines having such a need can include canines having diabetes, obesity, an inflammatory disease, a cardiovascular disease, a metabolic disorder, a musculoskeletal disorder, or cancer. In one aspect, modulating gastrointestinal microflora of the canine can be part of a treatment for diabetes, obesity, an inflammatory disease, a cardiovascular disease, a metabolic disorder, a musculoskeletal disorder, or cancer.

The present pet food compositions generally are complete and balanced pet foods for a canine. Additionally, the pet food compositions generally comprise protein and carbohydrates in amounts that can module the B/F ratio of a canine such that the ratio can be below 0.8. As discussed herein, generally, the protein content can be from about 25% to 60% of the pet food composition. In one aspect, the protein content can be from about 45% to about 60%. Additionally, the carbohydrate content can be from about 5% to about 30% of the pet food composition. In one aspect, the carbohydrate content can be from about 10% to about 20%.

As discussed herein, generally the pet food composition can include components that provide a B/F ratio of less than 0.8. In one aspect, the ratio can be below 0.7. In another aspect, the ratio can be below 0.6. In still another aspect, the ratio can be below 0.5.

Further, the pet food composition can comprise other components in order to provide the appropriate B/F ratio. In one embodiment, the pet food composition can comprise a probiotic that decreases *Bacteroidetes* microflora in the canine. In another embodiment, the pet food composition can comprise a probiotic that increases *Firmicutes* microflora. In some aspects, the pet food composition can comprise a probiotic that decreases *Bacteroidetes* microflora and a probiotic that increases *Firmicutes* microflora. While such probiotics can be components of the pet food composition, in one embodiment, the probiotic can be administered separately from the pet food composition. Additionally, in one aspect, the probiotic can be added to the pet food composition prior to administering. Additionally, the pet food composition can comprise a prebiotic.

The present pet food compositions are generally administered to the canine sufficient to modulate the B/F ratio to the desired level. Additionally, such administration can be performed in sufficient periods/frequencies to achieve a desired therapeutic effect. For example sufficient to treat diabetes, obesity, an inflammatory disease, a cardiovascular disease, a metabolic disorder, a musculoskeletal disorder, or cancer. In one aspect, the administration can be on a regular basis. In other aspects, the administration can be a long term administration or on an extended basis.

Typically, the methods and compositions discussed herein can provide a B/F ratio less than 0.8. Such B/F ratio can be calculated from the relative presence of *Streptococcus infantarius*, *Ruminococcus ruminococcus* sp., [*Clostridium*] *hiranonis*, *Clostridium perfringens*, *Enterococcus faecium*, [*Clostridium*] *bartlettii*, [*Clostridium*] *difficile*, [*Ruminococcus*] *gnavus*, *Lachnospiraceae* bacterium, *Blautia hansenii*, [*Ruminococcus*] *obeum*, *Faecalibacterium prausnitzii*, *Clostridium butyricum*, *Lactobacillus ruminis*, *Turicibacter sanguinis*, and *Lactobacillus acidophilus* from the *Firmicutes* phylum and *Bacteroides coprocola*, *Parabacteroides merdae*, *Bacteroides coprophilus*, *Prevotella copri*, and *Bacteroides bacteroides* sp. from the *Bacteroidetes* phylum.

In addition to the B/F ratio, the present compositions and methods can provide other beneficial effects. In one embodiment, after administration, *Lactobacillus ruminis* can be decreased by 25%. In other aspects, *Lactobacillus ruminis* can be decreased by 30%, 40%, 50%, 60%, 70%, 80%, 90%, or even 100%.

Generally, the methods and compositions described herein can provide an increase or a decrease in at least one of organic matter digestibility, dry matter digestibility, fiber digestibility, energy digestibility, fat digestibility or protein digestibility in the companion animal. In some embodiment, the increase or decrease can be at least 5%, 10%, 15%, 20%, 25%, 30%, 35%, 40%, 45%, or even 50%. In one aspect, the compositions and methods can provide an increase. In another aspect, the compositions and methods can provide a decrease.

In each of these compositions and methods, the pet food composition can be a wet food, a semi-moist food or a dry food. In an embodiment, the pet food composition can be one or more components of a blended composition. In some embodiments, the pet food composition is a kibble, and in some embodiments, the pet food composition is a meat analog.

The pet food compositions disclosed herein can be any food formulated for consumption by a canine. In an embodiment, the pet food composition provides complete nutrition as defined by the Association of American Feed Control Officials (AAFCO).

The pet food composition can comprise meat, such as emulsified meat. Examples of suitable meat include poultry, beef, pork, lamb and fish, especially those types of meats suitable for pets. The meat can include any additional parts of an animal including offal. Some or all of the meat can be provided as one or more meat meals, namely meat that has been dried and ground to form substantially uniform-sized particles and as defined by AAFCO. Additionally or alternatively, vegetable protein can be used, such as pea protein, corn protein (e.g., ground corn or corn gluten), wheat protein (e.g., ground wheat or wheat gluten), soy protein (e.g., soybean meal, soy concentrate, or soy isolate), rice protein (e.g., ground rice or rice gluten) and the like.

The pet food compositions disclosed herein can comprise vegetable oil, a flavorant, a colorant and water. Suitable vegetable oils include soybean oil, corn oil, cottonseed oil, sunflower oil, canola oil, peanut oil, safflower oil, and the like. Examples of suitable flavorants include yeast, tallow, rendered animal meals (e.g., poultry, beef, lamb, pork), flavor extracts or blends (e.g., grilled beef), animal digests, and the like. Suitable colorants include FD&C colors, such as blue no. 1, blue no. 2, green no. 3, red no. 3, red no. 40, yellow no. 5, yellow no. 6, and the like; natural colors, such as caramel coloring, annatto, chlorophyllin, cochineal, betanin, turmeric, saffron, paprika, lycopene, elderberry juice, pandan, butterfly pea and the like; titanium dioxide; and any suitable food colorant known to the skilled artisan.

The pet food compositions disclosed herein can optionally include additional ingredients, such as other grains and/or other starches additionally or alternatively to flour, amino acids, fibers, sugars, animal oils, aromas, other oils additionally or alternatively to vegetable oil, humectants, preservatives, polyols, salts, oral care ingredients, antioxidants, vitamins, minerals, probiotic microorganisms, bioactive molecules or combinations thereof.

Suitable starches include a grain such as corn, rice, wheat, barley, oats, soy and the like, and mixtures of these grains, and can be included at least partially in any flour. Suitable humectants include salt, sugars, propylene glycol and polyhydric glycols such as glycerin and sorbitol, and the like. Suitable oral care ingredients include alfalfa nutrient concentrate containing chlorophyll, sodium bicarbonate, phosphates (e.g., tricalcium phosphate, acid pyrophosphates, tetrasodium pyrophosphate, metaphosphates, and orthophosphates), peppermint, cloves, parsley, ginger and the like. Examples of suitable antioxidants include butylated hydroxyanisole ("BHA") and butylated hydroxytoluene ("BHT"), vitamin E (tocopherols), and the like.

Non-limiting examples of vitamins that can be used include Vitamins A, B-complex (such as B-1, B-2, B-6 and B-12), C, D, E and K, niacin and acid vitamins such as pantothenic acid and folic acid and biotin. Non-limiting examples of suitable minerals include calcium, iron, zinc, magnesium, iodine, copper, phosphorus, manganese, potassium, chromium, molybdenum, selenium, nickel, tin, silicon, vanadium, boron and the like.

As discussed herein, the compositions can further comprise prebiotics or probiotics. Probiotics are live microorganisms that have a beneficial effect in the prevention and treatment of specific medical conditions when ingested. Probiotics are believed to exert biological effects through a phenomenon known as colonization resistance. The probiotics facilitate a process whereby the indigenous anaerobic flora limits the concentration of potentially harmful (mostly aerobic) bacteria in the digestive tract. Other modes of action, such as supplying enzymes or influencing enzyme activity in the gastrointestinal tract, may also account for some of the other functions that have been attributed to probiotics. Prebiotics are nondigestible food ingredients that beneficially affect host health by selectively stimulating the growth and/or activity of bacteria in the colon. Prebiotics include fructooligosaccharides (FOS), xylooligosaccharides (XOS), galactooligosaccharides (GOS), and mannooligosaccharides (typically for non-human foods such as pet foods). The prebiotic, fructooligosaccharide (FOS) is found naturally in many foods such as wheat, onions, bananas, honey, garlic, and leeks. FOS can also be isolated from chicory root or synthesized enzymatically from sucrose. FOS fermentation in the colon results in a large number of physiologic effects including increasing the numbers of bifidobacteria in the colon, increasing calcium absorption, increasing fecal weight, shortening of gastrointestinal transit time, and possibly lowering blood lipid levels. Probiotics enhance systemic cellular immune responses and may be useful as a dietary supplement to boost natural immunity in otherwise healthy adults. Probiotics include many types of bacteria but generally are selected from four genera of bacteria: *Lactobacilllus acidophillus, Bifidobacteria, Lactococcus*, and *Pediococcus*. Beneficial species include *Enterococcus* and *Saccharomyces* species. The amount of probiotics and prebiotics to be administered to the animal is determined by the skilled artisan based upon the type and nature of the prebiotic and probiotic and the type and nature of the animal, e.g., the age, weight, general health, sex, extent of microbial depletion, presence of harmful bacteria, and diet of the animal. Generally, probiotics are administered to the animal in amounts of from about one to about twenty billion colony forming units (CFUs) per day for the healthy maintenance of intestinal microflora, and in one aspect, from about 5 billion to about 10 billion live bacteria per day. Generally, prebiotics are administered in amounts sufficient to positively stimulate the healthy microflora in the gut and cause these "good" bacteria to reproduce. As discussed herein, probiotics and/or prebiotics can be selected to provide a B/F ratio of less than 0.8/Typical amounts are from about one to about 10 grams per serving or from about 5% to about 40% of the recommended daily dietary fiber for an animal. The probiotics and prebiotics can be made part of the composition by any suitable means. Generally, the agents are mixed with the composition or applied to the surface of the composition, e.g., by sprinkling or spraying. When the agents are part of a kit, the agents can be admixed with other materials or in their own package.

Non-limiting examples of suitable preservatives include potassium sorbate, sorbic acid, sodium methyl para-hydroxybenzoate, calcium propionate, propionic acid, and combinations thereof.

Specific amounts for each additional ingredient in the pet food compositions disclosed herein will depend on a variety of factors such as the ingredient included in the first edible material and any second edible material; the species of animal; the animal's age, body weight, general health, sex, and diet; the animal's consumption rate; the purpose for which the food product is administered to the animal; and the like. Therefore, the components and their amounts may vary widely.

For example, the amount of any of the above-noted ingredients can be decreased or increased based on the estimated effect on one or more of diabetes, obesity, an inflammatory disease, a cardiovascular disease, a metabolic disorder, a musculoskeletal disorder, or cancer.

EXAMPLES

The following non-limiting examples are illustrative of embodiments of the present disclosure.

Example 1—Microflora Study of Canines

32 Beagles and 32 Labradors were selected with half obese/overweight and half lean/normal. All dogs were fed on base diet for 4 weeks (phase 1). Dogs were randomized into two dietary groups (Table 1—Study Design) based on age, sex, and body fat. Dogs were fed with either Diet A—High Protein, Low Carbohydrate (HPLC) or Diet B—Low Protein, High Carbohydrate (LPHC) for additional four weeks (phase 2). Fecal samples were collected at the end of each phase. Diets are provided in Table 2.

TABLE 1

| Dogs | | Pre-test (2-4 wks) | Phase I (4 wks) | Phase II (4 wks) |
|---|---|---|---|---|
| Labrador Retrievers (32) | Lean (16) body fat: <20% - females <17.5% - males | Base diet. Dogs in overweight cohort with BCS < 7 will be fed ad-lib until their BCS ≥ 7. All others fed once a day to maintain body weight. | Base diet. Daily feeding to maintain body weight | Diet A (8) Diet B (8) |
| | Overweight (16) body fat: >25%, preferably >30% | | | Diet A (8) Diet B (8) |
| Beagles (32) | Lean (16) | | | Diet A (8) Diet B (8) |
| | Overweight (16) body fat: >25%, preferably >30% | | | Diet A (8) Diet B (8) |

Base diet: Purina ® ProPlan ® Chicken and Rice; Diet A: High protein, low carbohydrate Diet B: High carbohydrate, low protein

TABLE 2

| Diet | Protein (Dry weight %) | Fat (Dry weight %) | Carbohydrates (Dry weight %) | Crude fiber (Dry weight %) |
|---|---|---|---|---|
| Base | 27.42 | 16.62 | 39.48 | 1.51 |
| A | 49.42 | 16.9 | 15.4 | 4.23 |
| B | 24.95 | 16 | 42.03 | 3.43 |

16S rRNA gene was sequenced for each sample. An average of 167,500 sequences were generated for each sample. Data processing and cleansing were performed using MOTHUR (version 1.34.3) (available from www-.mothur.org/). All sequences were converted to standard FASTA format. Two sets of paired sequences were aligned and joined into contigs. Sequences with ambiguous bases, shorter than 200 bp or longer than 500 bp, with homopolymer stretch longer than 8 bp, or those failed to align with the appropriate 16S rRNA variable region of the Silva bacterial reference sequences were eliminated. Sequences were then de-multiplexed by sample groups using barcode sequences. Samples with less than 8,000 sequences were not included in the analysis. Chimeric sequences generated due to PCR amplification of multiple sequences were removed using. Processed reads were then demultiplexed into barcode-indexed sample categories. Reads were clustered into operational taxonomic units (OTU) using a closed reference-based UCLUST (available from Drive 5 Bioinformatics software and services) algorithm at 97% sequence similarity level. Taxonomy was assigned using the predefined taxonomy map derived from the Greengenes database (August, 2013 release).

Dietary effects on intestinal fecal bacterial composition and abundance were visible through the PCA plot. Differentially abundant bacterial taxa (DAT) between the two dietary treatment groups were identified using linear discriminant analysis effect size (LEfSe) (Table 3). White's nonparametric t-test was also performed to identify additional DATs (Table 4) that were not present in Table 3. *Bacteroidetes* was overrepresented in LPHC diet group, while *Firmicutes* was overrepresented in HPLC diet group.

TABLE 3

| Phylum | Class | Order | Family | Genus | Species |
|---|---|---|---|---|---|
| *Bacteroidetes* | *Bacteroidia* | *Bacteroidales* | *Prevotellaceae* | *Prevotella* | *copri* |
| *Firmicutes* | *Bacilli* | *Lactobacillales* | *Lactobacillaceae* | *Lactobacillus* | *ruminis* |
| *Bacteroidetes* | *Bacteroidia* | *Bacteroidales* | *Bacteroidaceae* | *Bacteroides* | *plebeius* |
| Firmicutes | Bacilli | Lactobacillales | Streptococcaceae | Streptococcus | luteciae |
| Firmicutes | Clostridia | Clostridiales | Clostridiaceae | Clostridium | perfringens |
| Firmicutes | Clostridia | Clostridiales | Lachnospiraceae | [Ruminococcus] | gnavus |
| Firmicutes | Clostridia | Clostridiales | Lachnospiraceae | Blautia | producta |
| Firmicutes | Clostridia | Clostridiales | Lachnospiraceae | Clostridium | colinum |
| Firmicutes | Clostridia | Clostridiales | Peptostreptococcaceae | [Clostridium] | difficile |
| Firmicutes | Clostridia | Clostridiales | Clostridiaceae | Clostridium | hiranonis |
| *Bacteroidetes* | *Bacteroidia* | *Bacteroidales* | *[Paraprevotellaceae]* | *[Prevotella]* | |
| *Firmicutes* | *Bacilli* | *Turicibacterales* | *Turicibacteraceae* | *Turicibacter* | |
| *Bacteroidetes* | *Bacteroidia* | *Bacteroidales* | *Porphyromonadaceae* | *Parabacteroides* | |
| *Firmicutes* | *Clostridia* | *Clostridiales* | *Clostridiaceae* | *Clostridium* | |
| Firmicutes | Clostridia | Clostridiales | Clostridiaceae | SMB53 | |
| Firmicutes | Clostridia | Clostridiales | Lachnospiraceae | [Ruminococcus] | |
| Firmicutes | Clostridia | Clostridiales | Clostridiaceae | Clostridium | |
| Firmicutes | Bacilli | Lactobacillales | Streptococcaceae | Streptococcus | |
| Firmicutes | Clostridia | Clostridiales | Peptostreptococcaceae | [Clostridium] | |
| *Bacteroidetes* | *Bacteroidia* | *Bacteroidales* | *Prevotellaceae* | | |
| *Firmicutes* | *Bacilli* | *Turicibacterales* | *Turicibacteraceae* | | |
| *Bacteroidetes* | *Bacteroidia* | *Bacteroidales* | *Porphyromonadaceae* | | |
| Firmicutes | Clostridia | Clostridiales | Clostridiaceae | | |
| Firmicutes | Clostridia | Clostridiales | Peptostreptococcaceae | | |
| Firmicutes | Clostridia | Clostridiales | Lachnospiraceae | | |
| Firmicutes | Bacilli | Lactobacillales | Streptococcaceae | | |
| *Bacteroidetes* | *Bacteroidia* | *Bacteroidales* | | | |
| *Firmicutes* | *Bacilli* | *Turicibacterales* | | | |
| Firmicutes | Clostridia | Clostridiales | | | |
| *Bacteroidetes* | *Bacteroidia* | | | | |
| Firmicutes | Clostridia | | | | |
| *Bacteroidetes* | | | | | |
| Firmicutes | | | | | |

Table 3: Differentially abundant bacterial taxa identified using linear discriminant analysis effect size (LEfSe). Italicized Non-bolded names indicate increased abundance in LPHC diet, while bolded names indicate increased abundance in HPLC diet. Bacterial taxa were selected as DATs if the P is less than 0.01 and the linear discriminant analysis (LDA) score is greater than 3. Only bacteria in the phyla of *Bacteroidetes* and *Firmicutes* are listed.

TABLE 4

| Phylum | Class | Order | Family | Genus | Species |
|---|---|---|---|---|---|
| *Firmicutes* | *Clostridia* | *Clostridiales* | *Clostridiaceae* | *Clostridium* | *butyricum* |
| *Bacteroidetes* | *Bacteroidia* | *Bacteroidales* | *Bacteroidaceae* | *Bacteroides* | *coprophilus* |
| *Bacteroidetes* | *Bacteroidia* | *Bacteroidales* | *Porphyromonadaceae* | *Parabacteroides* | *distasonis* |
| *Bacteroidetes* | *Bacteroidia* | *Bacteroidales* | *Bacteroidaceae* | *Bacteroides* | *fragilis* |
| *Bacteroidetes* | *Bacteroidia* | *Bacteroidales* | *Bacteroidaceae* | *Bacteroides* | *uniformis* |
| Firmicutes | Clostridia | Clostridiales | Lachnospiraceae | [Ruminococcus] | torques |
| *Firmicutes* | *Clostridia* | *Clostridiales* | *Christensenellaceae* | *Christensenella* | |
| Firmicutes | Clostridia | Clostridiales | Clostridiaceae | SMB53 | |
| Firmicutes | Bacilli | Lactobacillales | Enterococcaceae | Vagococcus | |

TABLE 4-continued

| Phylum | Class | Order | Family | Genus | Species |
|---|---|---|---|---|---|
| Firmicutes | Bacilli | Lactobacillales | Leuconostocaceae | Weissella | |
| Bacteroidetes | Bacteroidia | Bacteroidales | [Paraprevotellaceae] | | |
| Firmicutes | Bacilli | Lactobacillales | Enterococcaceae | | |

Table 4: Additional differentially abundant bacterial taxa (DAT) identified using White's nonparametric t-test. DATs in Table 3 are not included. Non-bolded names indicate increased abundance in LPHC diet, while bolded names indicate increased abundance in HPLC diet. DATs with a p value less than 0.05 were selected. Only bacteria in the phyla of Bacteroidetes and Firmicutes are listed.

In addition, metagenome (whole bacterial genomes) was sequenced for each sample. An average of 11.8 gigabases of sequence was obtained for each sample. Data analysis using Gehan's test revealed DATs between the two dietary treatment groups (Table 5).

TABLE 5

| Phylum | Genus | Species |
|---|---|---|
| Bacteroidetes | | |
| Firmicutes | | |
| Bacteroidetes | Parabacteroides | |
| Firmicutes | Turicibacter | |
| Bacteroidetes | Prevotella | |
| Firmicutes | Streptococcus | |
| Firmicutes | Ruminococcus | |
| Firmicutes | Blautia | |
| Firmicutes | Enterococcus | |
| Firmicutes | Faecalibacterium | |
| Bacteroidetes | Parabacteroides | merdae |
| Bacteroidetes | Bacteroides | coprophilus |
| Firmicutes | Clostridium | butyricum |
| Firmicutes | Lactobacillus | ruminis |
| Firmicutes | Turicibacter | sanguinis |
| Bacteroidetes | Prevotella | copri |
| Firmicutes | Lactobacillus | acidophilus |
| Bacteroidetes | Bacteroides | Bacteroides sp. |
| Firmicutes | Streptococcus | infantarius |
| Firmicutes | Ruminococcus | Ruminococcussp. |
| Firmicutes | [Clostridium] | hiranonis |
| Firmicutes | Clostridium | perfringens |
| Firmicutes | Enterococcus | faecium |
| Firmicutes | [Clostridium] | bartlettii |
| Firmicutes | [Clostridium] | difficile |
| Firmicutes | [Ruminococcus] | gnavus |
| Firmicutes | Lachnospiraceae | bacterium |
| Bacteroidetes | Bacteroides | coprocola |
| Firmicutes | Blautia | hansenii |
| Firmicutes | [Ruminococcus] | obeum |
| Firmicutes | Faecalibacterium | prausnitzii |

Table 5: Differentially abundant bacterial taxa (DAT) identified in metagenomics study. Non-bolded names indicate increased abundance in LPHC diet, while bolded names indicate increased abundance in HPLC diet. DATs with a P value less than 0.05 were selected. Only bacteria in the phyla of Bacteroidetes and Firmicutes are listed.

The DATs identified in this study can be used as biomarkers for weight management study or for monitoring the therapeutic effect on obesity or other related conditions. Diets can also be formulated with prebiotic and/or probiotic to restore symbiosis as part of dietary treatment regimens for obesity based on the differential taxonomical profiles observed in obese vs. lean dogs.

As such, the present embodiments can include one or combination of the described DATs in Tables 3-5 to modulate the GI microbiota. As discussed herein, the B/F ratio can be used as a tool to monitor benefit of weight management study. Additionally, the presently described compositions and methods can use prebiotics and/or probiotics based upon the described DATs in Tables 3-5 to modulate the B/F ratio in the gut to gain the benefits on weight management conferred by the HPLC diet in pets.

In addition to the above, Lactobacillus ruminis was abundant in carbohydrate-rich diet fed dogs (LPHC or base diet), but was completely eradicated after feeding HPLC. As motile L. ruminis is considered pro-inflammatory, the present compositions and methods using a HPLC diet may exert its beneficial effect partially via eradicating pro-inflammatory bacteria such as L. ruminis. Additionally, the use of prebiotics, probiotics or other dietary compositions to suppress the growth of L. ruminis can help achieve the said beneficial effects from HPLC diet.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of modulating gastrointestinal microflora in a canine, comprising:
   administering to the canine a single pet food composition comprising from about 25% to about 60% protein, from about 5% to about 30% carbohydrates, fat, and fiber;
   wherein, after administration, the Bacteroidetes to Firmicutes (B/F) ratio of the canine is less than 0.8.

2. The method of claim 1, wherein the pet food composition comprises a first probiotic that decreases Bacteroidetes microflora in the canine.

3. The method of claim 2, wherein the pet food composition comprises a second probiotic that increases Firmicutes microflora.

4. The method of claim 1, wherein the pet food composition comprises a probiotic that increases Firmicutes microflora in the canine.

5. The method of claim 4, wherein the probiotic is administered separately from the pet food composition.

6. The method of claim 4, wherein the probiotic is added to the pet food composition prior to administering.

7. The method of claim 1, further comprising identifying the canine as having diabetes, obesity, an inflammatory disease, a cardiovascular disease, a metabolic disorder, a musculoskeletal disorder, or cancer.

8. The method of claim 1, wherein modulating gastrointestinal microflora of the canine is part of a treatment for diabetes, obesity, an inflammatory disease, a cardiovascular disease, a metabolic disorder, a musculoskeletal disorder, or cancer.

9. The method of claim 1, wherein the Bacteroidetes to Firmicutes ratio (B/F) ratio of the canine is less than 0.7.

10. The method of claim 1, wherein the pet food composition comprises from about 45% to about 60% protein.

11. The method of claim 1, wherein the pet food composition comprises from about 10% to about 20% carbohydrates.

12. The method of claim 1, wherein the pet food composition comprises a prebiotic.

13. The method of claim 1, wherein the administration is on a regular basis.

14. The method of claim 1, wherein B/F ratio is calculated from the presence of *Streptococcus infantarius, Ruminococcus ruminococcus* sp., *[Clostridium] hiranonis, Clostridium perfringens, Enterococcus faecium, [Clostridium] bartlettii, [Clostridium] difficile, [Ruminococcus] gnavus, Lachnospiraceae bacterium, Blautia hansenii, [Ruminococcus] obeum, Faecalibacterium prausnitzii, Clostridium butyricum, Lactobacillus ruminis, Turicibacter sanguinis,* and *Lactobacillus acidophilus* from the *Firmicutes* phylum and *Bacteroides coprocola, Parabacteroides merdae, Bacteroides coprophilus, Prevotella copri,* and *Bacteroides bacteroides* sp. from the *Bacteroidetes* phylum.

15. The method of claim 1, wherein, after administration, *Lactobacillus ruminis* is decreased by 25%.

* * * * *